United States Patent [19]
Stori

[11] Patent Number: 4,792,421
[45] Date of Patent: Dec. 20, 1988

[54] OXYGEN MOISTENING APPARATUS PROVIDED WITH A FLOW RATE ADJUSTING AND METERING DEVICE

[75] Inventor: Oreste Stori, Salo', Italy

[73] Assignee: Sio S.p.A.-Societa' per L'industria Dell'Ossigeno e di Altri Gas, Milan, Italy

[21] Appl. No.: 60,442

[22] Filed: Jun. 11, 1987

[30] Foreign Application Priority Data

Jun. 11, 1986 [IT] Italy .............................. 22231/86[U]

[51] Int. Cl.⁴ .............................................. A61M 51/00

[52] U.S. Cl. ................................ 261/122; 128/200.11; 128/203.12

[58] Field of Search .................... 128/203, 12, 203, 16, 128/200.11, 200.12; 261/77, 96, 122; 422/306

[56] References Cited

U.S. PATENT DOCUMENTS

| | | | |
|---|---|---|---|
| 1,897,403 | 2/1933 | Stephenson | 128/200.12 |
| 2,913,234 | 11/1959 | Beaurline | 261/77 X |
| 3,595,443 | 7/1971 | Jones | 261/77 X |
| 3,923,057 | 12/1975 | Cbalon | 128/203.16 |
| 4,261,933 | 4/1981 | Ewing | 261/122 |

*Primary Examiner*—Alan Cohan
*Attorney, Agent, or Firm*—Oblon, Fisher, Spivak, McClelland & Maier

[57] ABSTRACT

Oxygen moistening apparatus provided with a flow rate adjusting and measuring device comprising an at least partially transparent container the inside of which is tightly divided into two discrete chambers and which may be tightly closed by a cover member provided with an inlet hole and adapted for coupling to an oxygen delivery pipe communicating with an outlet hole opening to the first of the chambers. In the first chamber there is housed a flow rate measuring device communicating with a dipping tube having a free end and extending into the second chamber of the container with the free end located at the bottom of the container. From the bottom a collecting tube extends in the second chamber, having a free end and with its other end outwardly opening at a hole formed through the bottom of the container, a shut off manually operated valve being mounted on the cover member.

3 Claims, 1 Drawing Sheet

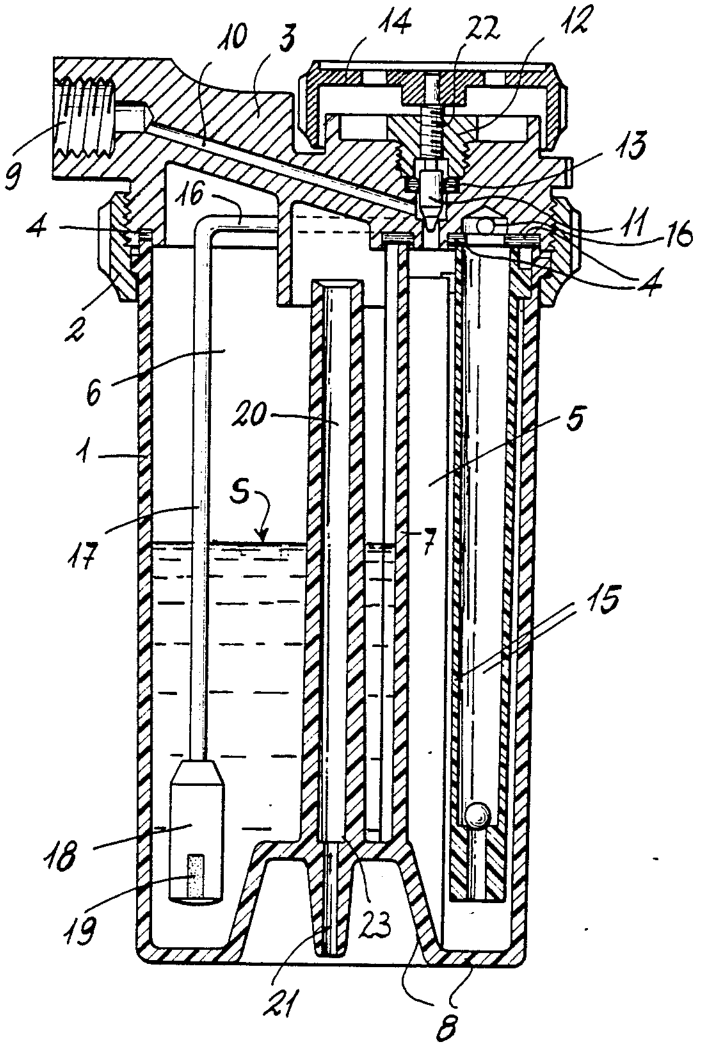
10
3
14
22
12
9
13
16
11
16
4
4
2
6
20
5
1
S
17
7
15
18
19
23
21
8

OXYGEN MOISTENING APPARATUS PROVIDED WITH A FLOW RATE ADJUSTING AND METERING DEVICE

FIELD OF THE INVENTION

The present invention relates to an oxygen moistening apparatus provided with a flow rate adjusting and measuring device.

BACKGROUND OF THE INVENTION

As is known, therapeutical use oxygen is administered to patients upon moistening by water. Presently the oxygen moistening operation is carried out by apparatuses including flow rate adjusting and measuring devices, which apparatuses are of comparatively large size, have poor handling characteristics, and are very expensive.

OBJECT OF THE INVENTION

The main object of the invention is to provide a therapeutical use oxygen moistening apparatus which is of very reduced size which is, of simple and easy operation, which is provided with a flow rate measuring device which is protected against possible damages, and which is particularly adapted for hospitals and home administering applications.

SUMMARY OF THE INVENTION

According to one aspect of the present invention, the above and other objects are achieved by an oxygen moistening apparatus characterized in that it comprises an at least partially transparent container the inside of which is tightly divided into two discrete chambers by means of a partition wall. The container can be tightly closed by a cover member provided with an inlet hole to be coupled to an oxygen delivery pipe. The oxygen delivery pipe communicates, through a first channel formed in the cover member, with an outlet hole opening to the first of the two chambers. In the first chamber a flow rate measuring device is housed, and oxygen is caused to pass through the flow rate measuring device. The first chamber communicates, through a second channel also formed in the cover member, with an elongated dipping tube having a free end. The dipping tube extends in the second of the two chambers with its free end located close to the bottom of the container. From the bottom of the container there extends in the second chamber a collecting tube one end of which is free and opens close to the cover member. The other end of the collecting tube opens outwardly at a hole formed through the bottom of the container. A filling member is provided for coupling to a moistened oxygen delivery pipe. On the cover member a manually operated shut off valve is mounted for adjusting the oxygen flow rate from the inlet hole to the outlet hole of the apparatus.

BRIEF DESCRIPTION OF THE DRAWING

In order to better understand the structure and characteristics of the oxygen moistening apparatus according to the present invention, a preferred embodiment thereof will be disclosed herein after with reference to the accompanying drawing, in which the oxygen moistening apparatus is schematically shown in a longitudinal cross-sectional view.

DESCRIPTION OF THE PREFERRED EMBODIMENT

In the drawing there is shown an oxygen moistening apparatus comprising a container 1 made of a transparent material and having a bell bottom 8. On the container 1 there is fixedly mounted, through a threaded ring nut 2, a cover member 3 which presses a tight gasket 4 against the free end of the container 1.

The container 1 is divided into two discrete chambers 5 and 6 by a partition wall 7 extending from the bell bottom 8. The top free edge of the partition wall 7 tightly engages with the gasket 4 pressed by the cover member 3.

The cover member 3 is provided with an inlet hole 9 adapted for coupling to an oxygen delivery pipe (not shown) (for example at a pressure from 3 to 4 bars). The inlet hole 9 communicates, through a first channel 10, with an outlet opening into the chamber 5. The first channel 10 is shut off by a pin 11 having a threaded portion thereof engaging in a threaded hole 22 of a gasket pusher 12 acting on an O-ring 13.

With the pin 11 a wheel 14 is rigid. The wheel 14 may be manually operated so as to vary the free passage of the first channel 10, thereby affording the possibility of easily adjusting (from a zero flow rate to a maximum flow rate) the oxygen amount passing through the first channel 10 in the time unit, as it should be apparent.

In the chamber 5 a flow rate measuring device 15 of know type is housed. The oxygen from the first channel 10 passes (from the bottom to the top as shown in the figure) through the flow rate measuring device. The oxygen exits at the top end of the flow rate measuring device 15, passes through a channel 16 formed in the cover member 3 (the channel 16 has been shown schematically in the drawing), and passes through an elongated dipping tube 17 the lower free end of which is provided with a cup 18. Windows are found in the cup 18, and a porous body 19 (also of known type) is housed in the cup 18. The oxygen is caused to pass through the porous body 19 so as to be dispersed in the water partially filling the chamber 6, there to be fractioned in small bubbles and moistened.

The thus mentioned oxygen bubbles are displaced above the water free surface S and pass, from the top to the bottom, through a collecting tube 20 the top free of which opens close to the cover member 3 and the lower end of which opens at a hole 23 formed through the bell bottom 8. At the hole 23 a lug 21 is provided. A duct (not shown) may be coupled to the lug 21 for conveying the moistened oxygen (for example with a flow rate of 0.5 to 6 liters per minute) to the user.

The disclosed apparatus is of the so-called "bubbling" type, in which oxygen is caused to pass through water. It should, however, be apparent that the apparatus would also be capable of operating in a water and the lower end of the pipe 17 is free—that is, devoid of the cup 18 housing the porous body 19.

From the above disclosure it should be apparent that the moistening apparatus structure and use are very simple and, accordingly, of very reduced cost. Thus the apparatus may be used in all of the places in which it will be necessary—for example, in hospitals, as well as at the user's home.

What we claim is:

1. An oxygen moistening apparatus provided with a flow rate adjusting and measuring device, said apparatus comprising:

(a) an at least partially transparent container the inside of which is tightly divided into two discrete chambers by means of a partition wall effective to be tightly closed by a cover member provided with an inlet hole to be coupled to an oxygen delivery pipe communicating, through a first channel formed in said cover member, with an outlet hole opening to the first of said two chambers;

(b) a flow rate measuring device housed in said first chamber for flow of oxygen therethrough communicating through a second channel formed in said cover member with an elongated dipping tube having a free end, said elongated dipping tube extending in the second of the two chambers with the free end located close to the bottom of said container;

(c) a collecting tube extending from the bottom of said second chamber, one end of said collecting tube being free and opening close to said cover member and the other end of said collecting tube opening outwardly at a hole formed through the bottom of said container;

(d) a member connected to said other end of said collecting tube for coupling to a moistened oxygen delivery pipe; and (e) a manually operated shut off valuve mounted on said cover member for adjusting the oxygen flow rate from said inlet hole to said outlet hole of said apparatus.

2. An apparatus according to claim 1, wherein said shut off valve comprises a pin extending in said first channel of said cover member, said pin being rigid with a small wheel which may be manually operated from outside, said pin having a threaded portion engaging in a threaded hole formed in said cover member or in a body affixed thereto.

3. An apparatus according to claim 1, wherein the free end of elongated dipping tube is provided with a cup including openings and housing a porous body, said second chamber being provided for holding water, and said apparatus being of the bubbling type.

* * * * *